(12) United States Patent
Martínez-Force et al.

(10) Patent No.: US 6,891,091 B2
(45) Date of Patent: May 10, 2005

(54) PLANT, SEEDS AND OIL WITH SATURATED TRIACYLGLYCEROL CONTENT AND OIL HAVING A HIGH STEARIC ACID CONTENT

(75) Inventors: Enrique Martínez-Force, Sevilla (ES); Valle Fernandez-Moya, Cordova (ES); Rafael Garcés, Sevilla (ES)

(73) Assignee: Consejo Superior de Investigaciones Cientificas, Sevilla (ES)

( * ) Notice: Subject to any disclaimer, the term of this patent is extended or adjusted under 35 U.S.C. 154(b) by 0 days.

(21) Appl. No.: 09/795,499

(22) Filed: Feb. 20, 2001

(65) Prior Publication Data

US 2002/0184673 A1 Dec. 5, 2002

Related U.S. Application Data

(63) Continuation-in-part of application No. 08/682,690, filed as application No. PCT/EP95/00369 on Jan. 31, 1995, now Pat. No. 6,410,831.

(30) Foreign Application Priority Data

| Jan. 31, 1994 | (ES) | 9400177 |
| Jan. 31, 1994 | (ES) | 9400178 |
| Jun. 24, 1994 | (ES) | 9401383 |
| Jun. 24, 1994 | (ES) | 9401384 |

(51) Int. Cl.$^7$ ............................. A01H 5/00; A01H 1/00
(52) U.S. Cl. ....................... 800/322; 800/264; 800/276
(58) Field of Search ............................. 800/322, 264, 800/276, 260, 274, 278; 426/601, 615; 435/419, 468

(56) References Cited

U.S. PATENT DOCUMENTS

| 4,378,655 | A | 4/1983 | Johnson |
| 4,388,339 | A | 6/1983 | Lomneth et al. |
| 4,390,561 | A | 6/1983 | Blair et al. |
| 4,447,462 | A | 5/1984 | Tafuri et al. |
| 4,627,192 | A | 12/1986 | Fick |
| 4,743,402 | A | 5/1988 | Fick |
| 5,786,019 | A | 7/1998 | Cain et al. |
| 6,022,577 | A | 2/2000 | Chrysam et al. |
| 6,277,433 | B1 | 8/2001 | Lantz et al. |
| 6,410,831 | B1 * | 6/2002 | Osorio et al. ............... 800/322 |

FOREIGN PATENT DOCUMENTS

| EP | 0 431 833 | 6/1991 |
| EP | 0 496 504 | 7/1992 |
| EP | 0 741 511 B1 | 9/1999 |
| JP | 02 039834 | 2/1990 |
| WO | WO 95/07620 | 3/1995 |
| WO | WO 95/20313 | 8/1995 |
| WO | WO 99/64546 | 12/1999 |
| WO | WO 01/05241 A1 | 1/2001 |

OTHER PUBLICATIONS

Bisplinghoff, F.D., "Quality Standard for Animal and Plant Fats," Fats and Proteins Research Foundation, Inc., Fort Myers Beach, Florida, Oct. 5, 1999.

Martinez–Force, E. et al., "Fatty Acid Composition in Developing High Saturated Sunflower (*Helianthus annuus*) Seeds: Maturation Changes and Temperature Effect," Instituto de la Grasa, CSIC, Sevilla, Spain, *J. Agric. Food Chem.* 46:3577–3582, 1998.

Osorio, J. et al., "Mutant Sunflowers with High Concentration of Saturated Fatty Acids in the Oil," *Crop Sci.* 35:739–742, 1995.

Purdy, R.H., Paper Entitled "Oxidative Stability of High Oleic Sunflower and Safflower Oils," pp. 523–525, Jun. 5, 1984.

Soldatov, K.I., "Chemical Mutagenesis in Sunflower Breeding," *Sunflower Convention in Krasnubar, USSR*, 1976.

\* cited by examiner

*Primary Examiner*—Elizabeth F. McElwain
(74) *Attorney, Agent, or Firm*—Christensen O'Connor Johnson Kindness PLLC

(57) ABSTRACT

The invention relates to a sunflower seed, comprising sunflower oil having increased stearic acid content as compared to wild type seeds preferably between 19.1 and 35% by weight related to the total amount of fatty acids in the oil, obtainable by treating parent seeds with a mutagenic agent during a period of time and in a concentration sufficient to induce one or more mutations in the genetic trait involved in stearic acid biosynthesis resulting in increased production of stearic acid, germinating the treated seeds and culturing progeny plants therefrom, collecting and analyzing progeny seeds, selecting seeds that have acquired the desirable genetic trait and optionally repeating the cycle of germination, culturing and collection of seeds. The invention further relates to oil extracted from the seeds, to a method for preparing the sunflower seeds, a method for preparing such sunflower oil, sunflower plants produced from the seeds and use of the oil.

4 Claims, No Drawings

PLANT, SEEDS AND OIL WITH SATURATED TRIACYLGLYCEROL CONTENT AND OIL HAVING A HIGH STEARIC ACID CONTENT

CROSS-REFERENCES TO RELATED APPLICATIONS

This is a continuation-in-part of U.S. application Ser. No. 08/682,690, filed Jul. 30, 1997, now U.S. Pat. No. 6,410,831, which is a 35 U.S.C. § 371 of International Application No. PCT/EP95/00369, filed Jan. 31, 1995,

FIELD OF THE INVENTION

The present invention relates to sunflower seeds comprising an oil having an increased stearic acid content as compared to wild type plants, namely, between 12% and 35% by weight related to the total amount of fatty acids in the oil. The invention also relates to sunflower seeds having a stearic acid content up to 54% by weight or more. The invention further relates to a sunflower oil extractable from the seeds of the invention, to sunflower plants produced from the seeds, to methods for preparing the seeds and the oil, as well as to the use of the oil in various products and to the products comprising the oil.

BACKGROUND OF THE INVENTION

Sunflowers are generally cultivated for obtaining oil which has saturated fatty acids (palmitic and stearic) and unsaturated fatty acids (oleic and linoleic). The stearic acid content is always less than 10% (F. D. Gustone, et al., *The Lipid Handbook*, Chapman and Hall, 1986), normally comprised between 3% and 7%. In relation to the unsaturated fatty acids, there are two different kinds of sunflower seeds: the normal sunflower which has a linoleic acid content between 50% and 70% (P. F. Knowles, "Recent Advances in Oil Crops Breeding, " *AOCS Proceedings* 1988) and the high oleic sunflower which has 2 to 10% of linoleic acid and 75 to 90% of oleic acid (K. I. Soldatov, "Chemical Mutagenesis in Sunflower Breeding," *Int. Proc. 7th Intern. Sunflower Conference*, 352–357, 1976). There is also a sunflower line having a high palmitic acid content, between 22% and 40% (R. Ivanov, et al., "Sunflower Breeding for High Palmitic Acid Content in the Oil," *Proc. of the 12th Intern. Sunflower Conference*, Vol. II, 453–465, 1988) and another line with low saturated fatty acid content (6% or less) (EP-A-496504).

Table 1 shows the fatty acid composition for some known sunflower oil varieties.

TABLE 1

| | % of fatty acids in sunflower oil | | | |
|---|---|---|---|---|
| Variety | Palmitic | Stearic | Oleic | Linoleic |
| Normal[1] | 5.9 | 5.7 | 21.8 | 66.5 |
| High Oleic[1] | 3.1 | 4.8 | 84.9 | 6.7 |
| Low Saturated[2] | 3.9 | 2.2 | 89.9 | 4.0 |
| High palmitic[3] | 25.1 | 4.3 | 10.6 | 56.4 |

[1]Fernández Martinez et al.; Grasas y Aceites 37 (1986)
[2]Patent EP-A-496504
[3]This variety has also 3.6% of palmitoleic acid The saturated fatty acid content of an oil is directly related to the physical and chemical characteristics thereof In case that said content is sufficiently high, the oil can be a solid at room temperature, like some animal fats. Normal sunflower oil is always a liquid under said conditions.

In the food industry, such as in the production of confectionery or margarine, animal fats or hydrogenated vegetable fats are usually used because a solid or semisolid product is required. By means of hydrogenation, unsaturated fatty acids are converted into saturated fatty acids. Animal fats as well as hydrogenated fats are not very recommendable from a nutritional point of view (C. K. Chow, *Fatty acids in food and their health implications*, Dekker, N.Y., 1992). Animal fats have a relatively high cholesterol content. Too much cholesterol in the diet may be detrimental to the health. Therefore, animal fats have been replaced in the last years with hydrogenated vegetable fats, which do not contain cholesterol.

However, said hydrogenated fats present another problem derived from the hydrogenation process. In said process, positional isomerization (shift of double bonds) and stereochemical transformations (formation of "trans" isomers) take place. Isomers are produced in an amount of up to 30% to 50% of the total fatty acids amount. These isomers are not very healthy from a nutritional point of view (R. Wood, *Biological effects of geometrical and positional isomers of monounsaturated fatty acids in humans*, Dekker, N.Y., 1990; W. C. Willet and A. Ascherio, "Trans Fatty Acids: Are the Effects Only Marginal?" *American Journal of Public Health*, Vol. 84, 5, 1994). Therefore, the use of hydrogenated fats in the food industry should be avoided.

Sunflower oil has a desirable content of unsaturated fatty acids. For use in the food industry however, the stearic acid content of the oil must be higher than in the normal sunflower oil (M. E. Norris, "Oil substitutions in food formulations," *Inform.* 1, 388–392, 1990) in order to obtain a more solid product.

It is thus an object of the present invention to provide a new, natural vegetable oil extracted from mutated seeds, the oil having a higher stearic acid content as compared to oil obtained from wild type seeds.

SUMMARY OF THE INVENTION

The present invention provides sunflower seeds, comprising a sunflower oil having an increased stearic acid content as compared to wild type seeds, obtainable by treating parent seeds with a mutagenic agent during a period of time and in a concentration sufficient to induce one or more mutations in the genetic trait involved in stearic acid biosynthesis, resulting in an increased production of stearic acid, germinating the treated seeds and culturing progeny plants therefrom, collecting and analyzing progeny seeds, selecting seeds that have acquired the desirable genetic trait and optionally repeating the cycle of germination, culturing and collection of seeds.

The present invention comprises a seed selected from a group consisting of CAS-3 and CAS-4 or their progeny which contains at least 12% stearic fatty acid by weight relative to the total amount of fatty acid in the oil, or a similar seed with contains at least 12% stearic fatty acid by weight relative to the total amount of fatty acid in the oil, further comprising an oil with at least 3.4% of the triacylglycerol species that have the general formula SMS and not more than 12.8% of triacylglycerol species that have the general formula SMM, wherein the formula gives from left to right the first, second and third fatty acid in the triacylglycerol and S represents a saturated fatty acid and M represents a monoenic fatty acid. The present invention further encompasses the oil extracted from such seed. Additionally, in yet another embodiment of the invention, the oil extracted from the seed comprises a stearic fatty acid content by weight which is not less than 15% of the total amount of fatty acids in the oil.

Additionally, in another embodiment of the invention, the seed further has an oil wherein less than 8.1% of triacylglycerol species have the general formula DDD.

The present invention further covers the oil extracted from the seeds which have CAS-3 or CAS-4 as an ancestor, which comprises triacylglycerol species in which at least 12.0% of the triacylglycerol species have the general formula SMS, and not more than 8.0% of triacylglycerol species having the general formula DDD, and the stearic fatty acid content by weight is not less than 12% of the total amount of fatty acid content of the oil. However, in certain embodiments, the oil extracted from the seeds has a stearic fatty acid content by weight of not less than 16% of the total amount of fatty acid content of the oil.

The invention includes an oil extracted from plant material with at least 3.4% of the triacylglycerol species that have the general formula SMS and not more than 12.8% of triacylglycerol species have the general formula SMM, wherein the formula gives from left to right the first, second and third fatty acid in the triacylglycerol and S represents a saturated fatty acid and M represents a monoenic fatty acid, and the oil contains at least 12% stearic fatty acid by weight relative to the total amount of fatty acid in the oil.

Additionally, another embodiment of the present invention is an oil extracted from seed comprising triacylglycerol species in which at least 12.0% of the triacylglycerol species have the general formula SMS, and not more than 8.0% of triacylglycerol species have the general formula DDD, and the stearic fatty acid content by weight is not less than 12% of the total amount of fatty acid content of the oil.

Preferably the sunflower seeds according to the invention comprise an oil having a stearic acid content of between 19.1 and 35% by weight, related to the total amount of fatty acids in the oil, and are obtainable by treating the parent seeds for 2 hours at room temperature with an alkylating agent, such as a solution of 70 mM ethyl methane sulfonate in water.

In another embodiment of the invention, the seeds comprise an oil having a stearic acid content of between 12 and 19% by weight related to the total amount of fatty acids in the oil, and are obtainable by treating the parent seeds with a solution of 2 mM sodium azide in water during 2 hours at room temperature.

Another object of the present invention is to provide a seed according to the invention designated CAS-3 or CAS-4, wherein representative seed of CAS-3 seed have been deposited under ATCC accession number 75968 and representative seed of CAS-4 seed have been deposited under ATCC accession number 75969. Additionally, the invention encompasses a sunflower plant or its parts, including but not limited to seeds, embryos and pollen, derived from such seed or from similar seed with the elevated stearic acid trait. And a seed having at least one of such sunflower as at least one ancestor sunflower plant. The invention further encompasses male sterile sunflower plant or its parts like its seeds derived from either of such seed and developed with germplasm comprising a cytoplasmic male sterility component. Or such a sunflower plant comprising a cytoplasmic male sterility restorer component.

Additionally, the present invention covers regenerable cells of these sunflower plants or their parts. Such material is often employed in the well-known process called transformation. During transformation at least one transgene is inserted into the sunflower material. The present invention covers the sunflower plant and its parts when at least some of the genetic material of the sunflower contains at least one transgene, regardless of whether the transgene was introduced by breeding or transformation processes directly. Examples of transgenes include herbicide-resistant genes, genes that inhibit sclerotinia with or without natural tolerance, and insect-resistant genes. The present invention also covers certain methods of developing a hybrid sunflower plant, comprising the steps of accessing sunflower material having the seed of CAS-3 or CAS-4, or similar seed with the high stearic acid trait as at least one ancestor, and crossing it with other different sunflower material wherein a hybrid sunflower plant is formed.

And the present invention covers a method of producing sunflowers comprising the steps of accessing sunflower material selected from the group consisting of inbred seed of CAS-3 or CAS-4 or similar seed with the high stearic acid trait, the sunflower plant produced thereof, or a sunflower plant having such seed as an ancestor, and breeding other sunflower material with the accessed plant or plant parts, wherein a different sunflower is produced than that of the original sunflower material.

DETAILED DESCRIPTION OF THE INVENTION

Sunflower seeds identified as "CAS-3" having an average stearic acid content of 25% by weight, related to the total amount of fatty acids in the oil, were deposited on Dec. 14, 1994, with the American Type Culture Collection, 12301 Parklawn Drive, Rockville, Md. 20852, U.S.A., under deposit accession number ATCC 75968. Sunflower seeds identified as "CAS-4" having an average stearic acid content of 15.4% by weight related to the total amount of fatty acids in the oil, were deposited on the same day with the same institution under deposit accession number ATCC 75969.

Seeds having an even higher stearic acid content between 29 and 54% by weight related to the total amount of fatty acids in the oil, may be obtained according to the invention by crossing sunflowers originating from seeds having a stearic acid content between 19.1 and 35% by weight with sunflowers originating from seeds having a stearic acid content between 12% and 19% by weight, and collecting the seeds.

The invention further relates to sunflower oil having a stearic acid content of between 12% and 54% by weight, preferably between 12% and 35% by weight, related to the total amount of fatty acids in the oil, which may be obtained by extracting sunflower seeds of the invention. Sunflower oil having a stearic acid content of 15.4% by weight related to the total amount of fatty acids in the oil, may be obtained by extracting sunflower seeds having the deposit accession number ATCC 75969. Sunflower oil having a stearic acid content of 25% by weight related to the total amount of fatty acids in the oil, is obtainable by extracting sunflower seeds having the deposit accession number ATCC 75968.

Preferably the sunflower oil of the invention has a palmitic acid content between 3 and 40% by weight, an oleic acid content between 3 and 85% by weight and a linoleic acid content between 2 and 84% by weight, all related to the total amount of fatty acids in the oil. Such types of oil may be obtained from seeds produced by crossing the high stearic acid seeds of the invention with seeds having a desirable content of one or more unsaturated and/or saturated fatty acids. Thus tailor-made seeds and tailor-made oil produced therefrom may be obtained by preparing mutants according to the invention and using these mutants in further conventional plant improvement practice by crossing them with other known or as yet unknown mutant or wild type plants.

The invention also relates to a method for preparing sunflower seeds having an increased stearic acid content as compared to wild type seeds, by treating parent seeds with a mutagenic agent during a period of time and in a concentration sufficient to induce one or more mutations in the genetic trait involved in stearic acid biosynthesis resulting in an increased production of stearic acid, germinating the treated seeds and culturing progeny plants therefrom, collecting and analyzing progeny seeds, selecting seeds that have acquired the desirable genetic trait and optionally repeating the cycle of germination, culturing and collection of seeds.

In practice the method comprises mutagenesis of sunflower seeds with a suitable mutagenic agent. The mutagenesis will produce inheritable genetic changes in the DNA of the seeds. According to the invention it was possible after several different treatments to select some treatments that produced a high number of genetic modifications in the genes that control the seed fatty acid biosynthesis. These treatments comprise the use of sodium azide or an alkylating agent, like ethyl methane sulfonate. Of course any other mutagenic agent having the same or similar effects may also be used.

Then, the next seed generation was analyzed with a new methodology described in R. Garcés and M. Mancha, "One-step lipid extraction and fatty acid methyl esters preparation from fresh plant tissues," *Analytical Biochemistry*, 211:139–143, 1993. This allowed for the detection of seeds with modifications in the composition of any fatty acid. Selected seeds showing a desirably high stearic acid content have been cultivated to the fifth generation, showing that this new genetic trait is inheritable and stable and independent of growth conditions.

In the method of the invention the parent seeds are, for example, treated during 2 hours at room temperature with a solution of 70 mM ethyl methane sulfonate in water, or during 2 hours at room temperature with a solution of 2 mM sodium azide in water.

In a further embodiment of the method of the invention, the mutation and selection steps may be followed by conventional plant improvement techniques, thus leading to seeds having, e.g., an even higher stearic acid content up to 54% by weight or more, or to seeds having a desirable content of one or more other fatty acids. In still another embodiment the seeds of the invention may be subjected to one or more further mutation treatments.

Sunflower oil having a stearic acid content of between 12 and 35% by weight, related to the total amount of fatty acids in the oil, may be prepared by extraction from sunflower seeds of the invention in any manner known to the person skilled in the art. Such extraction methods are well known and, for example, described in *Bailey's industrial oil and fat products*, Vol. 2, Chapter 3, 4$^{th}$ Ed., John Wiley and Sons, New York (1982).

The invention further relates to sunflower plants produced from seeds according to the invention. Thus, the seeds can be used to produce parent lines that have high stearic acid content in their oil. This also applies to plants originating from seeds obtained after crossing the mutants of the invention with each other or with other seeds having a desirable phenotype. The seeds may be cultured in the normal way on soil or any other substrate. The production of the modified plants does not require any additional measure as compared to the growing of ordinary sunflower seeds.

The sunflower plants may be used in breeding programmes for the development of sunflower lines or hybrids, which programmes are aimed at the production of open pollinated or hybrid varieties meeting the requirements of farming practice regarding yield, disease resistance and other agronomically important traits in major sunflower growing areas in the world. Seeds resulting from these programmes may be used in the growing of commercial sunflower crops.

The invention also relates to the use of a sunflower oil of the invention in the food industry. The natural vegetable oil that has been extracted from mutagenized sunflower seeds has a high stearic acid content between 12 and 35%, or in the case of intercrossing of the seeds, even up to 54% or more. This allows using the oil from these kinds of seeds as such. However, combinations of the oil of the invention with oil from the known high oleic acid or high palmitic acid sunflower seeds, in the production of edible fats or fat mixtures, like margarine, vegetable-dairy or in the production of confectionery or bakery is also possible depending on the requirements of the application. The advantage of these oils is that they do not have artificial fatty acid isomers, like the "trans" isomers found in the hydrogenated oils, and, of course, no cholesterol, like in the animal fats.

The invention further relates to products made by using the oil, such as margarine, vegetable-dairy, confectionery or bakery. The oil may simply replace oils or fats ordinarily used in those types of products. It is within the reach of the skilled person to determine how to use the oil without performing any inventive labor.

The present invention will be further illustrated by means of the following examples which are given for illustration purposes only and are in no way intended to limit the scope of the invention.

EXAMPLES

Materials and Methods

Sodium azide and ethyl methane sulfonate were used as mutagenic agents in Examples 1 and 2, respectively. Several sunflower lines with a stearic acid content between 12 and 35% have been obtained. In all these cases the original sunflower parent line used was RDF-1-532 (Sunflower Collection of Instituto de Agricultura Sostenible, CSIC, Córdoba, Spain) that has from 4 to 7% stearic acid content in the seed oil. The preparation of the lines CAS-3 and CAS-4, and of the line CAS-3×4 obtained after crossing CAS-3 with CAS-4, has been described in the following examples.

Example 1

Seeds were mutagenized with a solution of 70 mM of ethyl methane sulfonate (EMS) in water. The treatment was performed at room temperature during 2 hours while shaking (60 rpm). After mutagenesis the EMS solution was discarded and seeds were washed during 16 hours under tap water.

Treated seeds were germinated in the field and plants were self-pollinated. The seeds collected from these plants were used to select new sunflower lines with modifications in the fatty acid composition. By using the method of R. Garcés and M. Mancha, supra, the seed fatty acid composition was determined by gas liquid chromatography, after converting the fatty acids into their corresponding methyl esters.

A first plant with 9 to 17% stearic acid content in the oil was selected. The progeny were cultivated for five generations wherein the stearic acid content increased and the new genetic trait became stably fixed in the genetic material of the seed. This line is called CAS-3. A selected sample of this line was analyzed resulting in a stearic acid content of 26% (Table 2). The minimum and the maximum stearic acid content of the line were 19 and 35%, respectively. The stearic acid content of oil extracted from seeds from this cell line may thus lie between 19 and 35%.

Example 2

Sunflower seeds were mutagenized with sodium azide, at a concentration of 2 mM in water. The treatment was performed at room temperature during two hours while shaking (60 rpm). Then the mutagenesis solution was discarded and seeds were washed during 16 hours with tap water.

Seeds were planted in the field and plants were self-pollinated. Seeds from these plants were collected, and the fatty acid composition was determined by gas liquid chromatography, after converting the fatty acids into their corresponding methyl esters using the method described in Example 1.

Seeds from a plant having around 12% stearic acid in the oil were selected and cultivated for five generations. During this procedure the stearic acid content was increased and the new genetic trait fixed. This line is called CAS-4. A selected sample of this line was analyzed resulting in a stearic acid content of 16.1%. The minimum and the maximum values were 12 and 19%, respectively (Table 2).

TABLE 2

Percentage fatty acids

| Line | Palmitic | Stearic | Oleic | Linoleic |
|---|---|---|---|---|
| RDF-1-532 | 6.7 | 4.5 | 37.4 | 51.3 |
| CAS-3 | 5.1 | 26.0 | 13.8 | 55.1 |
| CAS-4 | 5.5 | 16.1 | 24.3 | 54.1 |

Example 3

Sunflower plants were grown from the sunflower seeds CAS-3 and CAS-4. The plants thus obtained were artificially pollinated in order to ensure only crossings between CAS-3 and CAS-4 to occur, not pollination of the mutant plants amongst themselves.

From the seeds thus produced plants were grown and the stearic acid content of the progeny was determined as described in Examples 1 and 2. Progeny and plants shall include plant cells, plant protoplasts, plant cell tissue cultures from which plants can be regenerated, plant calli, plant clumps, plant RNA and DNA and plant cells that are intact in plants or parts of plants, such as embryos, pollen, flowers, seeds, stamen, petals, leaves, hulls, stalks, roots, root tips, anthers, cells and the like, and this term also includes any transgenic DNA or (RNA) or portion thereof that have been introduced into the plant by whatever method. The hybrid CAS-3×4 had a stearic acid content of more than 35% by weight. From this it appears that intercrossing the mutants will yield hybrids with an even higher stearic acid content.

The oils contained within the seeds of CAS-3 and CAS-4 are triesters of glycerol with fatty acids and are called triglycerides or triacylglycerols (herein also identified as "TAG's"). The TAG of CAS-3 and CAS-4 are in a footprint that identified the oil. The three fatty acids within a triacylglycerol can be the same or different and may be either saturated or unsaturated. The physical properties of a triacylglycerol depend on its fatty acid composition. There are 3 positions in a TAG, sn-1, sn-2 and sn-3. The location of saturated fatty acids in the sn-2 position has been suggested to be responsible for the atherogenic effects of these acids. Thus TAG's with SMS and SDS are better, wherein the formula gives from left to rights the first, second and third fatty acid in the triacylglycerol and S represents a saturated fatty acid and M represents a monoenoic fatty acid and D represents a diunsaturated fatty acid.

The present invention provides a sunflower oil, which may be extracted from sunflower seeds and in which at least 3%, more preferable is over 5% of the triacylglycerol species that constitute the oil have a general formula SMS and preferably less than 25% and even more preferably less then 13.0% and yet even more preferred less then 6% of the triacylglycerol species have the general formula SMM.

In various embodiments of this invention the SDS TAG content of such an oil is usually higher than the SDS TAG content of normal sunflower oil. The present invention provides a sunflower oil, which may be extracted from sunflower seeds and in which at least 3%, more preferable at least 8% and even more preferably over 20% of the triacylglycerol species that constitute the oil have a general formula SDS, wherein the formula gives from left to right the first, second and third fatty acid in the triacylglycerol and S represents a saturated fatty acid and M represents a monoenoic fatty acid and D represents a diunsaturated fatty acid.

The oil according to the invention can be extracted from the mutant seeds deposited in the ATCC herein.

The oil of the invention is natural oil that can be extracted from the sunflower seeds and used directly without further modification methods to change the TAG content of the invention. Such modification method is for example so-called "hardening" of the oil, which means hydrogenation of fatty acids. The oil of the invention is obtained without performing such artificial modification processes.

The preferred sunflower oil of the invention has SMS levels of at least 3%. And the even more preferred sunflower oil of the present invention has SMS levels of less than 15%.

The saturated fatty acids as noted previously are stearic acid, palmitic acid, arachic acid and behenic acid. The oil must contain a relatively high stearic acid content so that the oil will preferably be semisolid at room temperature.

The triacylglycerol composition of the sunflower oil that can be extracted from normal seeds and the CAS-3 and the CAS-4 seeds on deposit is shown in Table 3, below. CAS-3 has no detectable amount of POP; 2% POE; EOE 4% (rounding to the nearest whole number); ELA=1%; PLP= 1%; PLE=7%; ELE=12%; POO=1%; EOO=4%. As noted in Table 3: P=palmitic; E=stearic; O=oleic; L=linoleic; A=arachic and B=behenic.

TABLE 3*

Triacylglycerol composition (%) of control normal sunflower oil and mutants CAS-3 and CAS-4

| TAG Species | Composition (%) | | |
|---|---|---|---|
|  | Normal | CAS-3 | CAS-4 |
| POP | 0.3 | — | — |
| PLP | 0.7 | 0.8 | — |
| POE | 0.5 | 2.1 | 1.5 |
| POO | 3 | 1 | 3.3 |
| PLE | 1.2 | 6.8 | 2.1 |
| POL | 7.4 | 3.3 | 5.1 |
| PLL | 6.1 | 4.8 | 3.5 |
| EOE | — | 3.6 | 1.9 |
| EOO | 2.2 | 4.1 | 8.6 |
| ELE | — | 12 | 1.8 |
| OOO | 6.4 |  | 9.4 |

TABLE 3*-continued

Triacylglycerol composition (%) of control
normal sunflower oil and mutants CAS-3 and CAS-4

| TAG Species | Composition (%) | | |
|---|---|---|---|
| | Normal | CAS-3 | CAS-4 |
| EOL | 5.2 | 14.6 | 12.1 |
| OOL | 18.8 | 2.7 | 15.7 |
| ELL | 5.2 | 24.6 | 9.1 |
| OLL | 26.8 | 6.5 | 15.3 |
| LLL | 14.8 | 7.6 | 8 |
| ELA | — | 1.1 | — |
| OLA | — | 0.8 | 0.7 |
| LLA | — | 1.2 | — |
| OOB | — | — | 0.9 |
| ELB | — | 0.7 | — |
| OLB | 0.5 | 0.8 | 1.1 |
| LLB | 0.6 | 0.9 | — |

*P = Palmitic; E = Stearic; O = Oleic; L = Linoleic; A = Arachic; B = Behenic

Table 4, below, shows the triacylglycerol composition (%) of a control normal sunflower oil (Normal) and mutants CAS-3 and CAS-4 according to the types of TAG.

TABLE 4*

Triacylglycerol composition (%) of a control sunflower oil
and mutants CAS-3 and CAS-4 according to types of TAG

| TAG Species | Composition (%) | | |
|---|---|---|---|
| | Normal | CAS-3 | CAS-4 |
| SMS | 0.8 | 5.7 | 3.4 |
| SMM | 5.2 | 5.1 | 12.8 |
| SDS | 1.9 | 21.4 | 3.9 |
| MMM | 6.4 | 0 | 9.4 |
| SDM | 13.1 | 19.5 | 19.0 |
| MDM | 18.8 | 2.7 | 15.7 |
| SDD | 11.9 | 31.5 | 12.6 |
| MDD | 26.8 | 6.5 | 15.3 |
| DDD | 14.8 | 7.6 | 8.0 |

*S = saturated (P, E, A, and B); M = monoenes (O); D = Dienes (L); where P = Palmitic; E = Stearic; O = Oleic; L = Linoleic; A = Arachic; B = Behenic The TAG's were analyzed using "Gas Liquid Chromatography"(GLC) in accordance with the techniques outlined in A. A. Carelli and A. Cert, "Comparative Study of the Determination of Triacylglycerol in Vegetable Oils using Chromatographic Techniques," *J. Chromatogr.*, 630:213–222 (1993).

As noted in Example 3 a hybrid of CAS-3 and CAS-4 (either can be the female plant) was produced, having a high level of stearic acid. Plants produced through the steps of accessing sunflower material having the seed of CAS-3 or CAS-4 or similar seed with the high stearic acid trait as at least one ancestor and crossing the plant grown form such seed with other different sunflower material wherein a hybrid sunflower plant is formed. Then the method can include the step of testing for the Tag or the oil or alternatively the first step of assessing the fatty acid content or a part of the fatty acid content of the oil. Then planting the selected seeds to form new lines and crossing those lines together or alternatively backcrossing to the parent or one of its progeny. Additionally, breeding pools can be employed to increase the variety of the traits. The resultant material is selected to have the elevated stearic acid and the TAG profile desired.

This TAG profile used for selection may be a number of TAG types such as SMS and SDS or it may simply be one TAG type such as SMS or DDD or the like. This is particularly true as processing methods exist for separation of TAG types often at relatively low cost. Allowing one portion of the oil to be extracted for use in a spread product like peanut butter and another portion of the oil to be employed in a lubrication type product or a liquid non semisolid type product such as cooking oil.

Possibly additional testing and plant selection through the further generations could reduce the SNM levels of the TAG. Alternatively if the SMS and SDS TAG is the useful portion, the TAG's could be separated by heat or cold processes.

Thus the preferred oil TAG has high levels of stearic fatty acid and a TAG with increased SMS compared to wild type oil and SDS also increased over the normal sunflower oil and SMM preferably below 25% and more preferable at or below 13% and even more preferred at or below the level in the wild type (normal sunflower).

The present invention can be employed to develop lines, open pollinated sunflower varieties or hybrid sunflowers. These sunflower plants can be used to produce new inbred lines by successive selfing and selection or by successive backcrossing. Conventional a line takes preferably three or more generations of selfing until the lines are fixed or true breeding.

Once lines are fixed, lines can be employed to form hybrids. Hybrids often employ a cytoplasmic male sterility (CMS) system. One line is most often crossed with CMS germplasm such as CMS HA89 (U.S. Department of Agriculture). The CMS germplasm is usually used in a breeding program with recurrent backcrosses to the line having the desired stearic acid percent. The final CMS progeny are virtually identical to the recurrent high level stearic acid parent except the CMS progeny is male sterile and does produce viable pollen. This CMS line is then crossed with the male parent that carries the genetic determinant encoding the fertility restorer of the male sterile cytoplasm (the restorer (R) line). This cross produces fertile pollen producing hybrid sunflower seeds. Other methods of sterility can also be employed, such as chemical gametocides.

The hybrid seed is then used to produce plants that yield seed that is "grain" and is crushed for its oil and meal or used for further breeding purposes.

According to the invention sunflower plants and seeds from which said oil can be extracted have been obtained by means of a biotechnological process. This high stearic acid content is an inheritable trait and is independent from the growing conditions.

While the preferred embodiment of the invention has been illustrated and described, it will be appreciated that various changes can be made therein without departing from the spirit and scope of the invention.

What is claimed is:

1. A method for producing sunflower seed having a desirable triacylglycerol profile, comprising:

(a) treating parent sunflower seed with a mutagenic agent during a period of time and in a concentration sufficient to induce one or more mutations in the genetic trait involved in stearic acid biosynthesis;

(b) germinating the treated parent seed of step (a) and culturing progeny plants therefrom;

(c) selecting progeny sunflower seed from the progeny plants of step (b) comprising an oil in which at least 3.4% of the triacylglycerol species in the oil have the formula SMS, not more than 12.8% of the triacylglycerol species in the oil have the formula SMM, and the oil comprises at least 12% stearic acid by weight relative to the total amount of fatty acids in the oil, wherein the formulae denote from left to right the first, second, and third fatty acid in the triacylglycerol, S represents a saturated fatty acid, and M represents a monoenic fatty acid;

(d) germinating the selected seed of step (c) and culturing progeny plants therefrom; and (e) collecting seed from the plants of step (d) or their progeny having the triacylglycerol profile of the seed of step (c).

2. The method of claim 1, wherein less than 8.0% of triacylglycerol species in the oil have the formula DDD, wherein D represents a dienic fatty acid.

3. A method of producing hybrid sunflower seeds having a desirable triacylglycerol profile, comprising:

(a) treating parent sunflower seed with a mutagenic agent during a period of time and in a concentration sufficient to induce one or more mutations in the genetic trait involved in stearic acid biosynthesis;

(b) germinating the treated parent seed of step (a) and culturing progeny plants therefrom;

(c) selecting progeny sunflower seed from the progeny plants of step (b) comprising an oil in which at least 3.4% of the triacylglycerol species in the oil have the formula SMS, not more than 12.8% of the triacylglycerol species in the oil have the formula SMM, and the oil comprises at least 12% stearic acid by weight relative to the total amount of fatty acids in the oil, wherein the formulae denote from left to right the first, second, and third fatty acid in the triacylglycerol, S represents a saturated fatty acid, and M represents a monoenic fatty acid;

(d) germinating the selected seed of step (c) and culturing progeny plants therefrom;

(e) collecting seed having the triacylglycerol profile of the seed of step (c) from the plants of step (d) or their progeny;

(f) germinating the collected seed of step (e) and culturing progeny plants therefrom; and (g) crossing the plants of step (f) with a second sunflower plant to produce hybrid sunflower seed.

4. The method of claim 3, wherein less than 8.0% of triacylglycerol species in the oil have the formula DDD, wherein D represents a dienic fatty acid.

* * * * *

UNITED STATES PATENT AND TRADEMARK OFFICE
CERTIFICATE OF CORRECTION

PATENT NO. : 6,891,091 B2
DATED : May 10, 2005
INVENTOR(S) : E. Martínez-Force et al.

It is certified that error appears in the above-identified patent and that said Letters Patent is hereby corrected as shown below:

Title page,
Item [12], "Martínez-Force et al." should read -- Martinez-Force et al. --; and
Item [75], Inventors, "Fernandez-Moya, Cordova" should read -- Fernández-Moya, Córdoba --.

Column 1,
Line 10, "1995," should read -- 1995. --.
Line 62, "thereof In" should read -- thereof. In --.

Column 10,
Line 9, "SNM" should read -- SMM --.

Signed and Sealed this

Thirteenth Day of September, 2005

JON W. DUDAS
*Director of the United States Patent and Trademark Office*